(12) United States Patent
Lin et al.

(10) Patent No.: US 8,883,491 B2
(45) Date of Patent: Nov. 11, 2014

(54) SYSTEMS AND METHODS FOR COUNTING CELLS AND BIOMOLECULES

(75) Inventors: Bo Lin, Lexington, MA (US); Peter Y. Li, Andover, MA (US); Jean Qiu, Andover, MA (US); Timothy Smith, Dracut, MA (US); Todd Sobolewski, Windham, NH (US); Alnoor Pirani, Allston, MA (US)

(73) Assignee: Nexcelom Bioscience LLC, Lawrence, MA (US)

( * ) Notice: Subject to any disclaimer, the term of this patent is extended or adjusted under 35 U.S.C. 154(b) by 303 days.

(21) Appl. No.: 12/935,973

(22) PCT Filed: Apr. 8, 2009

(86) PCT No.: PCT/US2009/039863
§ 371 (c)(1),
(2), (4) Date: Jan. 10, 2011

(87) PCT Pub. No.: WO2009/126685
PCT Pub. Date: Oct. 15, 2009

(65) Prior Publication Data
US 2011/0136152 A1    Jun. 9, 2011

(51) Int. Cl.
| | | |
|---|---|---|
| *G01N 21/00* | (2006.01) | |
| *C12M 1/34* | (2006.01) | |
| *G01N 21/76* | (2006.01) | |
| *G01N 15/14* | (2006.01) | |
| *G01N 21/64* | (2006.01) | |
| *G01N 15/10* | (2006.01) | |

(52) U.S. Cl.
CPC .... *G01N 15/1475* (2013.01); *G01N 2015/1006* (2013.01); *G01N 21/64* (2013.01); *G01N 21/6458* (2013.01); *G01N 2015/1486* (2013.01); *G01N 2015/1493* (2013.01)
USPC ....... 435/288.7; 435/7.2; 435/7.21; 435/7.23; 435/7.24; 435/40.51; 435/287.1; 435/287.6; 436/546; 436/10; 436/63; 436/164; 436/172; 422/400; 422/401; 422/403; 422/73

(58) Field of Classification Search
USPC .................. 435/7.1, 7.2, 287.2, 287.6, 288.7, 435/7.21–7.25, 40.5, 40.51, 287.1; 436/546, 10, 56, 63, 164, 172; 422/400, 401, 403, 73, 554, 417
See application file for complete search history.

(56) References Cited

U.S. PATENT DOCUMENTS

| | | | |
|---|---|---|---|
| 6,974,692 B2 * | 12/2005 | Chang ........................ | 435/288.3 |
| 2003/0231791 A1 * | 12/2003 | Torre-Bueno et al. ........ | 382/133 |
| 2004/0076319 A1 * | 4/2004 | Fauver et al. ................. | 382/133 |
| 2006/0094109 A1 * | 5/2006 | Trainer ....................... | 435/288.7 |
| 2011/0136152 A1 * | 6/2011 | Lin et al. ..................... | 435/7.25 |

* cited by examiner

*Primary Examiner* — Gail R Gabel
(74) *Attorney, Agent, or Firm* — Milstein Zhang & Wu LLC

(57) ABSTRACT

The present invention generally relates to systems and methods for counting biomolecules or cells. In certain embodiments, the invention provides a cell counting or biomolecule counting system including: a covered chamber having a known height and configured to hold a suspension of biomolecules or cells in a sample; at least one fluorescent light source connected to at least one fluorescent light beam narrowing device; a bright-field light source connected to a bright-field light beam narrowing device; a microscope objective; a detection device; a fluorescent filter assembly to allow only excitation light to illuminate the sample and allow only emission light from the sample to be imaged by the detection device; and a movable light shutter to block bright-field light during fluorescent detection.

17 Claims, 10 Drawing Sheets

SYSTEMS AND METHODS FOR COUNTING CELLS AND BIOMOLECULES

RELATED APPLICATION

The present application is the national phase of PCT/US2009/039863 having the international filing date of Apr. 8, 2009.

TECHNICAL FIELD

The present invention generally relates to systems and methods for counting cells and biomolecules.

BACKGROUND

Detection, identification, quantification, and characterization of biomolecules or cells of interest, such as stem cells or cancer cells, through testing of biological samples is an important aspect in the fields of medical diagnostics and medical research. Biological solutions, such as blood, spinal fluid, cell culture and urine, are routinely analyzed for their microscopic particle concentrations.

As an example, for determining cell concentrations in biological solutions, a commonly used method is to spread a cell-containing solution into a thin layer without cell overlap in the vertical direction. A precise volume is determined by keeping the height of the solution at a known constant level. Cells are viewed under an optical microscope and enumerated in defined areas. To eliminate the variation caused by microscopes, an area-defining grid is preferred in the counting chamber. A commonly used cell counting device is called hemacytometer, as disclosed in Risch (U.S. Pat. No. 1,693,961) and Hausser et al. (U.S. Pat. No. 2,039,219).

More recently, cell counting has been accomplished using flow cytometry, a technique for counting, examining, and sorting microscopic particles suspended in a stream of fluid. A beam of light, e.g., laser light, of a single wavelength is directed onto a hydro-dynamically focused stream of fluid. A number of detectors are aimed at a point where the stream passes through the light beam; one in line with the light beam and several perpendicular to it. Each suspended particle passing through the beam scatters the light in some way, and fluorescent chemicals found in the particle or attached to the particle may be excited into emitting light at a higher wavelength than the light source. This combination of scattered and fluorescent light is picked up by the detectors, and by analyzing fluctuations in brightness at each detector it is then possible to derive various types of information about the physical and chemical structure of each individual particle. Some flow cytometers on the market have eliminated the need for fluorescence and use only light scatter for measurement. Other flow cytometers form images of fluorescence, scattered light, and transmitted light for each cell.

In addition to prohibitive cost ($150,000 to $500,000) for a flow cytometry system, there are many technical problems associated with flow cytometry. For example, many technical problems result from cells clumping and clogging or sticking in the nozzle of the flow cytometer, causing the stream of fluid to deflect and become misaligned with the optics. Also, resulting aerosolization of the sample prevents biohazardous samples, e.g. human blood cells potentially infected with HIV or hepatitis virus, from being sorted unless stringent precautions are taken.

Further, flow cytometry can only provide an indirect measure of cell concentration and cell size. Flow cytometry relies on mixing a sample with a known concentration of beads, determining the number of beads that pass the detector in the flow cytometer, and correlating the bead count with the number of cells that pass the detector to determine the concentration of cells in the sample.

There is an unmet need for efficient and cost-effective systems and methods for counting biomolecules and cells.

SUMMARY

The present invention overcomes problems associated with flow cytometry by providing a cell counting system that takes images of a static population of cells in a sample that has been loaded into a chamber having a fixed height. Because the system utilizes a covered chamber having a fixed height, cell concentration can be determined from the cell count. Further, systems of the invention can provide a direct measurement of cell concentration and cell size without the need for beads, as is required in flow cytometry. The present invention provides capability for detecting, identifying, quantifying, and characterizing cells of interest without many of the technical problems associated with flow cytometry, and for significantly less costs.

An exemplary cell counting system of the invention includes: a covered chamber having a known height and configured to hold a suspension of biomolecules or cells in a sample; at least one fluorescent light source connected to at least one fluorescent light beam narrowing device; a bright-field light source connected to a bright-field light beam narrowing device; a microscope objective; a detection device; a fluorescent filter assembly to allow excitation light to illuminate the sample and to allow only the emission light from the sample to be imaged by the detection device; and a movable light shutter to block bright-field light during fluorescent detection.

Another exemplary cell counting system of the invention includes: a closed chamber configured to hold a suspension of biomolecules or cells in a sample, and to allow calculation of a volume of sample that is interrogated; at least one fluorescent light source connected to at least one fluorescent light beam narrowing device; a bright-field light source connected to a bright-field light beam narrowing device; a microscope objective; a detection device; a fluorescent filter assembly to allow only excitation light to illuminate the sample and allow only emission light from the sample to be imaged by the detection device; and a movable light shutter to block bright-field light during fluorescent detection.

The systems can be operably connected to a computer having cell counting analysis software installed on it. The fluorescent light beam and/or the bright-field light beam narrowing devices can be collimators. The fluorescent light source and the bright-field light source can be light emitting diodes. The detection device can be a camera, for example a charge-coupled device or CCD camera which may include a thermoelectric cooling capacity. The covered chamber can include a sample introduction port and an air escape port and a counting grid. In certain embodiments, the counting grid is an integral part of a top of the chamber. Alternatively, the counting grid is an integral part of a bottom of the chamber. The width of lines of the counting grid can range from about 0.1 micrometer to about 1 mm. The width of lines of the counting grid can range from about 1 micrometer to about 25 micrometer. The thickness of lines of the counting grid can range from about 0.1 micrometer to about 50 micrometer.

The system can be configured to capture the entirety of the sample with a single image. Alternatively, the system can be configured to capture a portion of the sample with a single image.

The sample can be a human or animal tissue or body fluid or a sample originated from a plant or living organism. For example, the sample can be serum, cell culture supernatant, or cell lysis. The biomolecules can be DNA, RNA, or protein. The biomolecule or cell can be indicative of a disease or disease state.

Another aspect of the invention provides a method for determining a concentration or number count of cells that express a biomarker in a population of cells in a sample including: contacting a sample comprising cells that express a biomarker with a fluorescently labeled agent that specifically binds the biomarker; loading the sample into a covered chamber having a known height, in which the population of cells is suspended within the chamber; acquiring a single static bright-field image of the population of cells in the sample in the chamber; acquiring a single static fluorescent image of the population of cells in the sample in the chamber; and comparing cell count from the bright-field image to cell count from the fluorescent image to determine the concentration or number count of the cells that express the biomarker in the population of cells. Prior to the loading step, the method can further include contacting the population of cells with an agent that makes the population of cells permeable.

The biomarker can be a cell surface biomarker. Alternatively, the biomarker can be an intercellular biomarker. The fluorescently labeled agent can be a fluorescently labeled antibody that possesses an epitope for the biomarker. The biomarker can be associated with a particular disease or disease state.

Another aspect of the invention provides a method for determining a concentration or number count of stem cells in a population of cells in a sample including: contacting a sample including stem cells with a fluorescently labeled agent that specifically binds the stem cells in the sample; loading the sample into a covered chamber having a known height, in which the population of cells is suspended within the chamber; acquiring a single static bright-field image of the population of cells in the sample in the chamber; acquiring a single static fluorescent image of the population of cells in the sample in the chamber; and comparing cell count from the bright-field image to cell count from the fluorescent image to determine the concentration or number count of stem cells in the population of cells.

The fluorescently labeled agent can be a fluorescently labeled antibody specific for a stem cell biomarker, or a particle coated with a fluorescently labeled antibody specific for a stem cell biomarker. Exemplary stem cell biomarkers include TRA-1-81, TRA-1-60, Thy-1, SSEA-3, SSEA4, Oct-4, CD9, CD30, and alkaline phosphatase.

Another aspect of the invention provides a method for determining infection rates of malaria including: contacting a sample of red blood cells from a subject having malaria with a fluorescently labeled agent specific for the malaria parasite; loading the sample into a covered chamber having a known height, in which the cells are suspended within the chamber; acquiring a single static bright-field image of the cells in the sample in the chamber; acquiring a single static fluorescent image of the cells in the sample in the chamber; and comparing cell count from the bright-field image to cell count from the fluorescent image to determine the infection rate of malaria in the subject.

Another aspect of the invention provides a method for identifying adipocytes in a sample including: contacting a sample including adipocytes with a fluorescently labeled agent that specifically binds the adipocytes; loading the sample into a covered chamber having a known height, in which the cells are suspended within the chamber; acquiring a single static bright-field image in the chamber of the sample; acquiring a single static fluorescent image in the chamber of the sample; and comparing the bright-field image to the fluorescent image to identify the adipocytes.

Another aspect of the invention provides a method for detecting a biomolecule in a sample including: contacting a sample with particles coated with a biotinylated antibody, and streptavidin coupled to a fluorescent indicator; loading the sample into a covered chamber having a known height, in which the biomolecules are suspended within the chamber; acquiring a single static bright-field image of the sample in the chamber; acquiring a static fluorescent image of the sample in the chamber; and comparing the bright-field image to the fluorescent image to detect the biomolecule in the sample. Prior to acquiring the bright-field image, the method can further include washing unbound particles. The biomolecule can be associated with a particular disease or disease state.

Another aspect of the invention provides a method for determining a concentration or number count of viable hepatocytes in a population of hepatocytes in a sample including: contacting a sample including hepatocytes with at least one fluorescently labeled agent; loading the sample into a covered chamber having a known height, in which the population of hepatocytes is suspended within the chamber; acquiring two or more static images of the population of hepatocytes, in which the first and second image are selected from the group consisting of a bright-field image, a fluorescent image of viable hepatocytes, and a fluorescent image of dead hepatocytes, in which the first image is different from the second image; comparing cell count from the first image to cell count from the second image to determine the concentration or number count of viable hepatocytes in the population of hepatocytes.

The population of hepatocytes can be contacted with two different fluorescent agents. A first fluorescent agent specifically binds viable hepatocytes, and a second fluorescent agent specifically binds dead hepatocytes. The first fluorescent agent can be acridine orange and the second fluorescent agent can be propidium iodine.

The first image can be the fluorescent image of live hepatocytes, the second image can be the fluorescent image of dead hepatocytes, and the concentration of viable hepatocytes in the population of hepatocytes can be determined by comparing cell count from the fluorescent image of live hepatocytes to cell count from the fluorescent image of dead hepatocytes. Alternatively, the first image can be the bright-field image, the second image can be the fluorescent image of dead hepatocytes, and the concentration of viable hepatocytes in the population of hepatocytes can be determined by comparing cell count from the bright-field image to cell count from the fluorescent image of dead hepatocytes. Alternatively, the first image can be the bright-field image, the second image can be the fluorescent image of live hepatocytes, and the concentration of viable hepatocytes in the population of hepatocytes can be determined by comparing cell count from the bright-field image to cell count from the fluorescent image of live hepatocytes.

In these methods, each of the single static bright-field image and the single static fluorescent image can be an image of the entire sample. Alternatively, each of the single static bright-field image and the single static fluorescent image can be an image of a portion of the sample. A single image refers to a non-scanning image. A single image includes multiple images of the same frame to be used for analysis, e.g., for obtaining an average.

DETAILED DESCRIPTION

Figure 1:
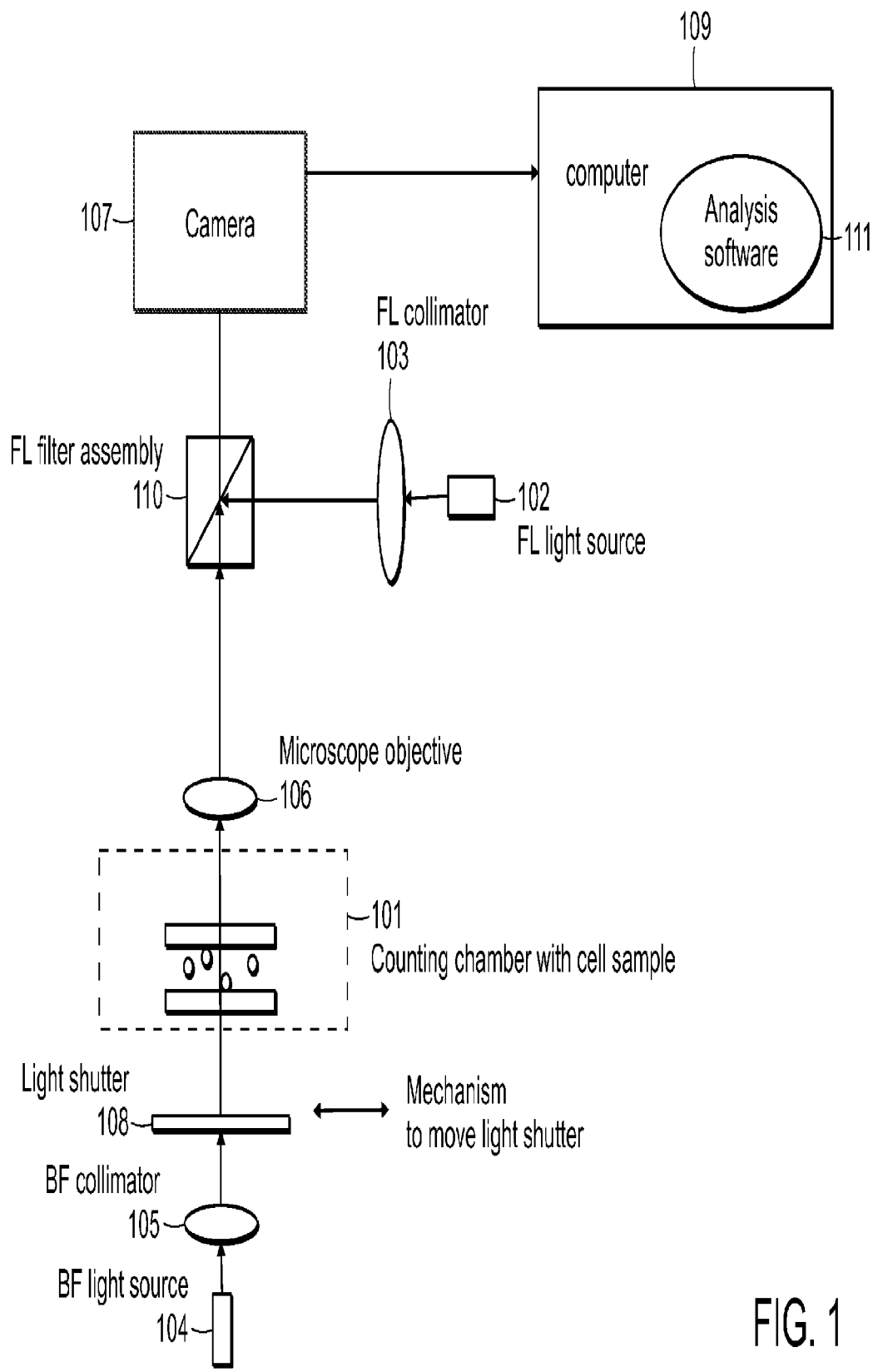
FIG. 1 is a schematic diagram of an embodiment of a cell counting and analysis system of the invention.

The biological mechanisms of many diseases have been clarified by microscopic examination of tissue samples or body fluids. Histopathological examination has also permitted the development of effective medical treatments for a variety of illnesses. In standard anatomical pathology, a diagnosis is made on the basis of cell morphology and staining characteristics. Tumor samples, for example, can be examined to characterize the tumor type and suggest whether the patient will respond to a particular form of chemotherapy. Microscopic examination and classification of tissue samples stained by standard methods (such as hematoxylin and eosin) has improved cancer treatment significantly.

Recent advances in molecular medicine have provided an even greater opportunity to understand the cellular mechanisms of disease, and select appropriate treatments with the greatest likelihood of success. For example, some hormone dependent breast tumor cells have an increased expression of estrogen receptors indicating that the patient from whom the tumor was taken will likely respond to certain anti-estrogen drug treatments. Other diagnostic and prognostic cellular changes include the presence of tumor specific cell surface antigens (as in melanoma), the production of embryonic proteins (such as carcinoembryonic glycoprotein antigen produced by gastrointestinal tumors), and genetic abnormalities (such as activated oncogenes in tumors). A variety of techniques have evolved to detect the presence of these cellular abnormalities, including immunophenotyping with monoclonal antibodies, in situ hybridization using nucleic acid probes, and DNA amplification using the polymerase chain reaction (PCR).

Effective use of such biomarkers in assisting in the diagnosis and identification of an effective therapeutic regimen has been impeded by the inability of current automated analysis systems to utilize and identify the varied biomarkers in a cost efficient, time sensitive, and reproducible manner. Thus, previous techniques and systems have often proven inadequate for the efficient analysis of tissue samples requiring a rapid parallel analysis of a variety of independent microscopic, histologic and/or molecular characteristics.

Additionally, manual methods can be extremely time consuming and can require a high degree of professional training to identify and/or quantify cells. This is not only true for tumor cell identification and detection, but also for other applications ranging from neutrophil alkaline phosphatase assays, reticulocyte counting and maturation assessment, and others. The associated manual labor leads to a high cost for these procedures in addition to the potential errors that can arise from long, tedious manual examinations.

The present invention provides capability for detecting, identifying, quantifying, and characterizing cells and biomolecules of interest. The present invention generally relates to systems and methods for counting cells and biomolecules in a sample. A sample includes biological materials obtained from or derived from a living organism. Typically the sample will include cells, tissue, or biomolecules, such as proteins, polynucleotides (e.g., DNA or RNA), organic material, and any combination of the foregoing. Such samples include, but are not limited to, hair, skin, tissue, cultured cells, cultured cell media, and body fluids.

A tissue is a mass of connected cells and/or extracellular matrix material, e.g., CNS tissue, neural tissue, eye tissue, liver tissue, placental tissue, mammary gland tissue, gastrointestinal tissue, musculoskeletal tissue, genitourinary tissue, and the like, derived from, for example, a human or other mammal and includes the connecting material and the liquid material in association with the cells and/or tissues. A body fluid is a liquid material derived from, for example, a human or other mammal. Such body fluids include, but are not limited to, blood, plasma, serum, serum derivatives, bile, phlegm, saliva, sweat, amniotic fluid, mammary fluid, and cerebrospinal fluid (CSF), such as lumbar or ventricular CSF. A sample also may be media containing cells or biological material.

Systems of the invention can also be used to interrogate cell lines. Cell lines refer to specific cells that can grow indefinitely given the appropriate medium and conditions. Systems of the invention can be used to interrogate any type of cell line. Cell lines can be mammalian cell lines, insect cell lines or plant cell lines. Exemplary cell lines can include tumor cell lines or stem cell lines.

Referring to FIG. 1, provided is a schematic diagram of an embodiment of a cell counting system 100 of the invention. Counting system 100 includes a covered counting chamber 101 having a known height and configured to hold a suspension of biomolecules or cells in a sample. Because the counting chamber has a known height, there is a known amount under interrogation, and a concentration of cells in the sample can be determined by calculating the area under interrogation with the known height of the chamber (which together define a volume of the sample under interrogation). An exemplary counting chamber, and methods of making such a chamber is shown in Qiu (U.S. patent application number 2004/0145805). The chamber can include a sample introduction port and an air escape port for ease of loading the chamber. The chamber can also include a counting grid for focusing and ease of cell. Exemplary counting grids are shown in Qiu (U.S. Pat. No. 7,329,537 and U.S. patent application number 2004/0145805).

The cell counting system 100 further includes at least one fluorescent light (FL) source 102 connected to at least one fluorescent light beam narrowing device 103. The system 100 also includes a bright-field (BF) light source 104 connected to a bright-field light beam narrowing device 105. The fluorescent light source and the bright-field light source can be a light emitting diode. The fluorescent light beam narrowing device and the bright-field light beam narrowing device can be a collimator.

The cell counting system 100 further includes a microscope objective 106, a detection device 107, and a movable light shutter 108. The detection device can be camera, such as a CCD camera, for acquiring images. The camera can be fitted with a cooling capability. In certain embodiments, microscope objective movements are under the control of a computer 109 operably connected to the system 100. In other embodiments, the microscope objective is fixed. The system 100 further includes a fluorescent filter assembly 110 to allow excitation light from the fluorescent light source 102 to illuminate the sample in the chamber 101, and to allow only the emission light from the sample to be imaged by the detection device 107. The system 100 also includes a movable light shutter 108 to block bright-field light during fluorescent detection.

The counting chamber 101 has a known height that may be pre-selected, adjusted, or fixed. The counting chamber 101 is covered or otherwise closed such that the suspension of sample therein would not lose volume due to evaporation. The chamber 101 is loaded with a sample by pipetting the sample into the sample introduction port of the chamber 101. As the sample is loaded into the chamber, air escapes the chamber 101 through the air escape port in the chamber 101. An exemplary sample size is 20 μl. Once the chamber 101 is loaded with the sample, the chamber 101 is loaded into the counting system 100 through a slot in a housing of the system.

Once an image is taken, the sample volume under interrogation can be obtained from the height of the counting chamber, and the area of the sample that is imaged. Thus, the interrogated sample volume can be obtained and is known for each image taken. It should be noted that the chamber height may be varied from application to application as long as the interrogated sample volume can be obtained or is known.

System 100 is configured for bright-field imaging and fluorescent images of the sample in the chamber 101. The components of the cell counting system 100 are encased in a housing. The bright-field light source 104 is positioned at the base of the housing and is configured to emit light onto the sample in the chamber 101 positioned in-line above the bright-field light source 104. Between the chamber 101 and the bright-field light source 104 is a bright-field light beam narrowing device 105. The beam narrowing device focuses the light emitted from the bright-field light source 104, and directed the light onto the sample in the chamber 101. Also positioned between the chamber 101 and the bright-field light source 104 is a movable light shutter 108. The movable light shutter 108 is located above the bright-field light beam narrowing device 105 and below the chamber 101. The light shutter 108 is connected to a mechanism for moving the shutter, such as a motor or a solenoid. The light shutter 108 is mechanically moved out of line with the bright-field light source 104 to allow the light from the bright-field light source 104 to interact with the sample in the chamber 101 during bright-field imaging. The light shutter 108 is mechanically moved in-line with the bright-field light source 104 to block the light from the bright-field light source 104 from interacting with the sample in the chamber 101 during fluorescent imaging.

After the light from the bright-field light source 104 passes through the sample in the chamber 101, the light subsequently passes through the microscope objective 106. The microscope objective 106 is responsible for primary image formation and is involved in determining quality of images that the system 100 is capable of producing. Microscope objective 106 is also involved in determining the magnification of a particular sample and the resolution under which fine sample detail can be observed in the system 100. Microscope objectives are commercially available from Olympus America Inc. (Center Valley, Pa.).

After the light from the bright-field light source 104 passes through the microscope objective 106, the emitted light from the sample passes through a fluorescent filter assembly 110, and the emitted light from the sample in the chamber 101 is acquired by the detection device 107. The fluorescent filter assembly 110 is in-line with the bright-field light source 104, the bright-field beam narrowing device 105, the chamber 101, the microscope objective 106, and the detection device 107. The fluorescent filter assembly 110 ensures that only emission light from the sample in the chamber 101 is imaged on the detection device 107. An exemplary detection device is a CCD camera commercially available from Olympus America Inc. (Center Valley, Pa.). The image from the detection device 107 is transmitted to a computer 109 having analysis software 111.

The system further includes at least one fluorescent light source 102 for fluorescent imaging of the sample in the chamber 101. When certain compounds are illuminated with high energy light (excitation light), they emit light of a different lower frequency. The fluorescent light source 102 is out of line with the bright-field light source 104, the bright-field beam narrowing device 105, the chamber 101, the microscope objective 106, and the detection device 107. The fluorescent light source 102 emits excitation light through a fluorescent beam narrowing device 103 to the fluorescent filter assembly 110. The fluorescent filter assembly 110 re-directs the excitation light from the fluorescent light source 102 to the sample in the chamber 101. The excitation light illuminates the sample in the chamber 101, and emitted light from the sample passes through the fluorescent filter 110 and is acquired by the detection device 107. The fluorescent filter 110 ensures that only the excitation light from the fluorescent light source 102 illuminates the sample in the chamber 101, and that only the emitted light from the sample in the chamber is imaged by the detection device 107.

Even though FIG. 1 shows only one set of fluorescent light source, fluorescent beam narrowing device, and fluorescent filter assembly, two or more sets of fluorescent light source, fluorescent beam narrowing device, and fluorescent filter assembly can be used for fluorescence excitation and emission detection. With two or more sets of fluorescence excitation and emission available on the same sample, more than one fluorescent label may be used for advanced assays.

During fluorescent detection, the light shutter 108 is mechanically moved in-line with the bright-field light source 104 to block the white light from the bright-field light source 104 from interacting with the sample in the chamber 101 during fluorescent imaging.

Figure 2:
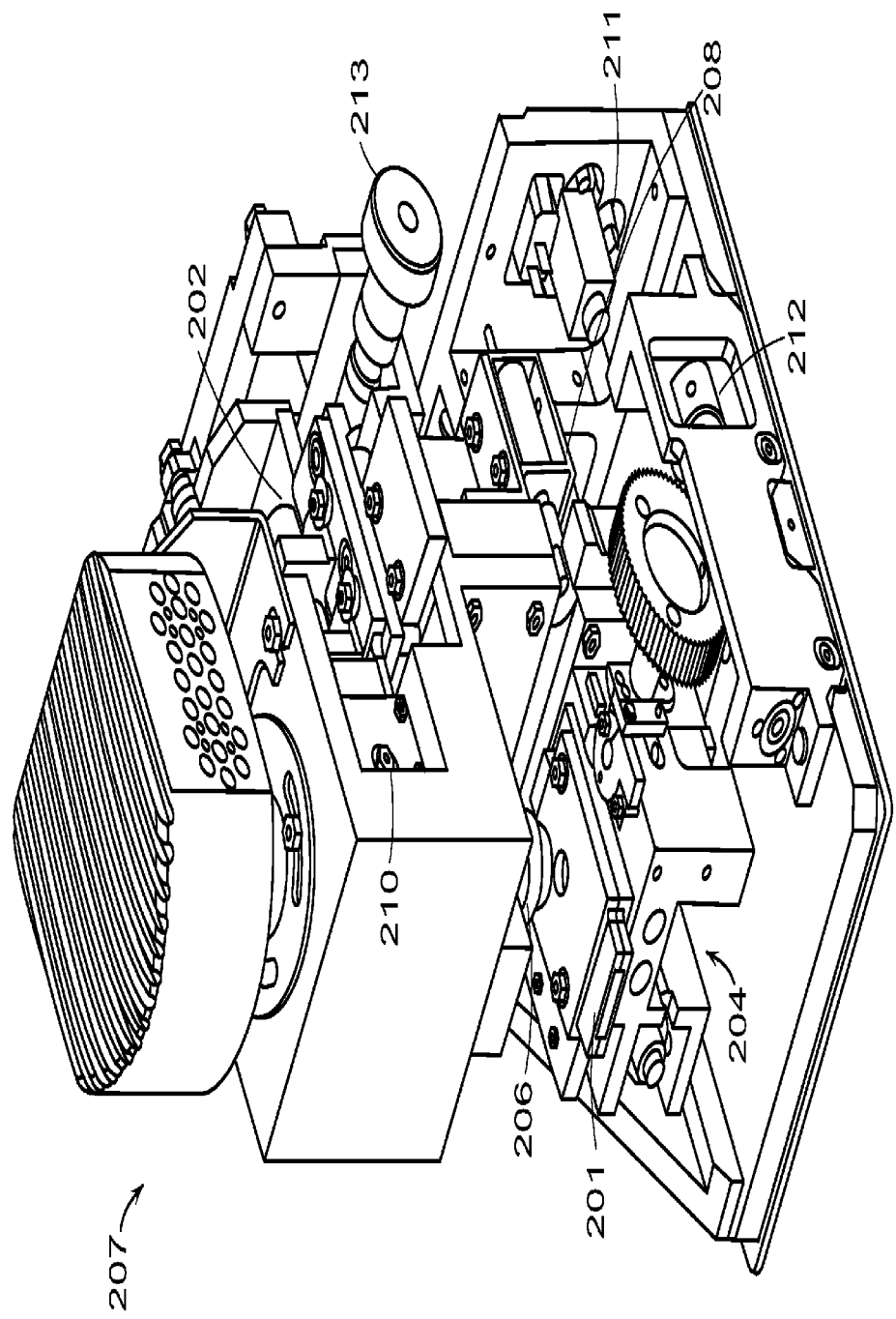
FIG. 2 is a drawing of an embodiment of an exemplary system with design details of certain components.

FIGS. 2-5 are drawings showing different views and component of the cell counting system of the invention with the housing removed. FIG. 2 shows a cell counting system 200. The counting chamber 201 containing a sample is loaded into system 200. The bright-field light source 204 and the bright-field beam narrowing device 205, shown as a collimator, are shown positioned in-line and below the sample chamber 201. The microscope objective 206 is shown positioned above the chamber 201 and in-line with the chamber 201, bright-field light source 204, and the bright-field beam narrowing device 205. The fluorescent filter assembly 210 is shown positioned above the microscope objective 206 and in-line with the microscope objective 206, the chamber 201, the bright-field light source 204, and the bright-field beam narrowing device 205. The detection device 207, shown as a CCD camera, is positioned above the fluorescent filter assembly 210, and in-line with the fluorescent filter assembly 210, the microscope objective 206, the chamber 201, the bright-field light source 204, and the bright-field beam narrowing device 205.

FIG. 2 also shows the fluorescent light source 202 and the fluorescent beam narrowing device 203, shown as a collimator. This figure shows that the fluorescent light source 202 and the fluorescent beam narrowing device 203 are out of line with the detection device 207, the fluorescent filter assembly 210, the microscope objective 206, the chamber 201, the bright-field light source 204, and the bright-field beam narrowing device 205. Fluorescent light source 202 is positioned to emit excitation light through the fluorescent beam narrowing device 203 and onto the fluorescent filter assembly 210. FIG. 2 also shows the position of the movable light shutter 208 and the mechanism for moving the shutter, such as a motor or a solenoid, to which it is connected.

This figure further shows the outlet plug 211 for connecting the system 200 to an external power supply. Also shown is a focus adjustment device 212 for focusing the microscope objective 206. The focusing device is shown as a wheel, and can be manually adjusted until optimal focusing of the cells or biomolecules in the sample. Also shown is a fluorescent channel switcher 213, for switching fluorescent channels in embodiments in which two or more sets of fluorescent light source, fluorescent beam narrowing device, and fluorescent filter assembly are used for fluorescence excitation and emission detection. With two or more sets of fluorescence excitation and emission available on the same sample, more than one fluorescent label may be used for advanced assays.

Figure 3:
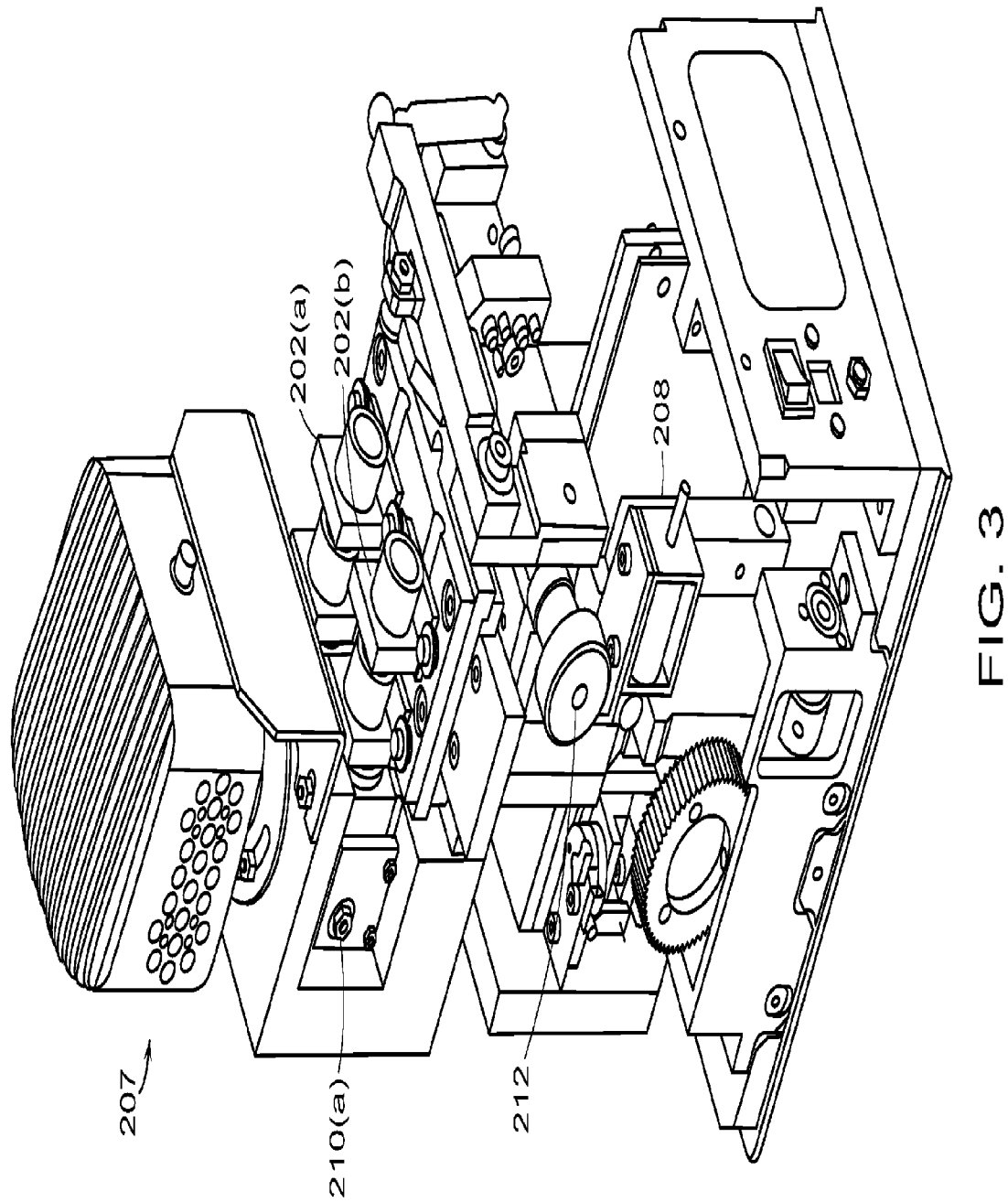
FIG. 3 is a drawing of an embodiment of an exemplary system depicting the bright-field and fluorescent light sources, collimators, and filter assemblies for fluorescent detection.
Figure 4:
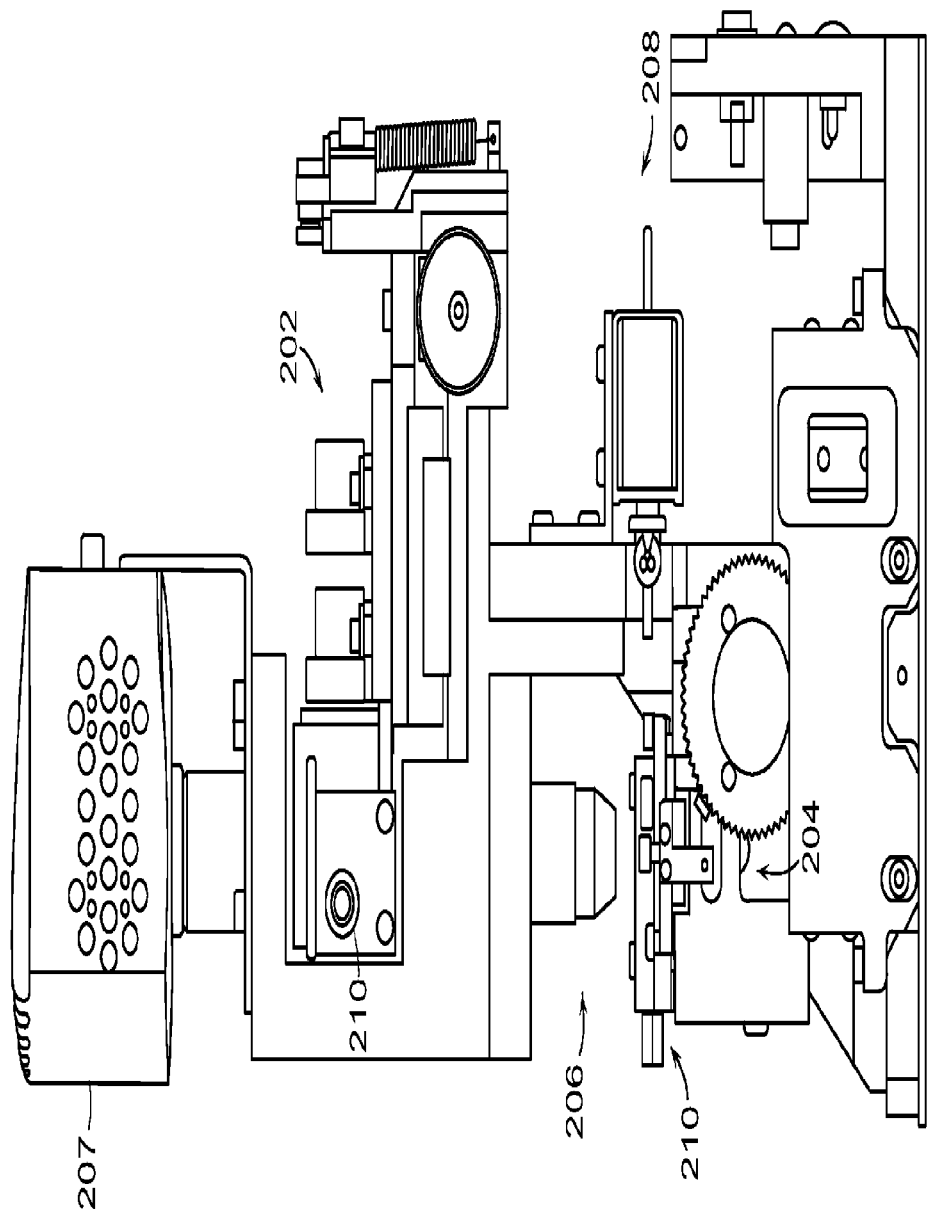
FIG. 4 is a drawing depicting certain components of an exemplary system.
Figure 5:
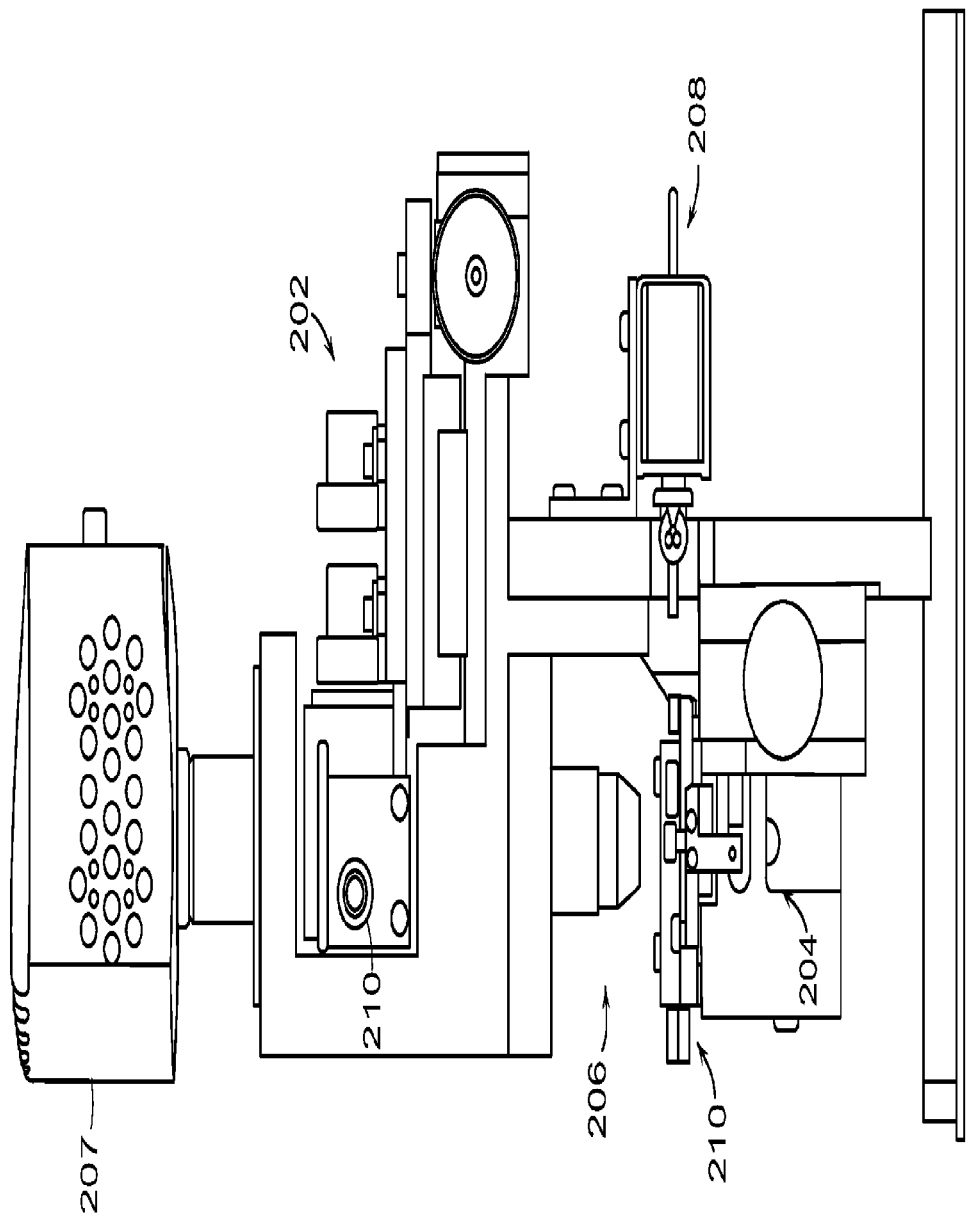
FIG. 5 is a drawing depicting certain components of an exemplary system.

FIGS. 3-5 depict the system described in FIGS. 1-2 from different orientations as shown in FIGS. 1-2. In these views, the fluorescent light source 202 and the fluorescent beam narrowing device 203 are more easily seen. In this figure, the system 200 is shown with two sets of fluorescent light source, fluorescent beam narrowing device, and fluorescent filter assembly for fluorescence excitation and emission detection (202(a) and (202(b)). This view further depicts the alignment of the fluorescent light source 202 and the fluorescent beam narrowing device 203 with the fluorescent filter assembly 210. Also shown is the fluorescent channel switcher 212 and the associated mechanics for selecting a set of fluorescent light source 202 and the fluorescent beam narrowing device 203. Also shown in the detection device 207 and the movable light shutter 208 along with the mechanics for moving the light shutter.

The cell counting system described herein captures bright-field and fluorescent images of cells or biomolecules in the chamber, analyzes the number of cells or biomolecules, sizes and fluorescent intensity of each cell, and then converts this data to concentration, size and fluorescence histograms and scatter plots. The cell counting system of the invention is useful for various biological assays and other applications. Determining Concentration or Number Count of Cells that Express a Biomarker Biomarkers are involved in cellular functions, cell proliferation, differentiation, migration, host defense, etc. Biomarkers can be cell surface biomarkers or can be intracellular biomarkers. Understanding and identifying biomarkers and quantifying the concentration of a biomarker in a population of cells will provide enormous opportunities for biomedical researchers to develop more effective therapeutic medicines to prevent, treat, and cure diseases.

A biomarker can be any cell component present in a sample that is identifiable by known microscopic, histologic, or molecular biology techniques. Biomarkers can be used, for example, to distinguish neoplastic tissue from non-neoplastic tissue. Such markers can also be used to identify a molecular basis of a disease or disorder including a neoplastic disease or disorder. Such a biomarker can be, for example, a molecule present on a cell surface, an over-expressed target protein, a nucleic acid mutation or a morphological characteristic of a cell present in a sample.

The methods of the invention involve contacting a sample including cells that express a biomarker with a fluorescently labeled agent that specifically binds the biomarker. If the biomarker is a cell surface biomarker, no further steps are required prior to contacting the sample with the fluorescently labeled agent. If the biomarker is an intracellular biomarker, cells of the sample can first be made permeable prior to contacting the cells with the fluorescently labeled agent.

A variety of agents are useful in determining and analyzing cellular molecules and mechanisms. Such agents include, for example, polynucleotides, polypeptides, small molecules, and/or antibodies useful in in situ screening assays for detecting molecules that specifically bind to a biomarker present in a sample. An agent can be detectably labeled such that the agent is detectable when bound or hybridized to its target biomarker or ligand. Detectably labeling any of the foregoing agents includes an enzymatic, fluorescent, or radionuclide label. Other reporter methods and labels are well known in the art.

An agent useful in the methods of the invention can be an antibody. Antibodies useful in the methods of the invention include intact polyclonal or monoclonal antibodies, as well as fragments thereof, such as Fab and $F(ab')_2$. For example, monoclonal antibodies are made from antigen containing fragments of a protein by methods well known to those skilled in the art (Kohler, et al., Nature, 256:495, 1975; and Harlow et al., Antibodies, Cold Spring Harbor Laboratory, pp. 93-117, 1988). Fluorescent molecules may be bound to an immunoglobulin either directly or indirectly by using an intermediate functional group.

An agent useful in the methods of the invention can also be a nucleic acid molecule (e.g., an oligonucleotide or polynucleotide). For example, in situ nucleic acid hybridization techniques are well known in the art and can be used to identify a RNA or DNA biomarker present in a sample. Screening procedures that rely on nucleic acid hybridization make it possible to identify a biomarker from any sample, provided the appropriate oligonucleotide or polynucleotide agent is available. For example, oligonucleotide agents, which can correspond to a part of a sequence encoding a target polypeptide (e.g., a cancer marker comprising a polypeptide), can be synthesized chemically or designed through molecular biology techniques. The polynucleotide encoding the target polypeptide can be deduced from the genetic code, however, the degeneracy of the code must be taken into account. For such screening, hybridization is typically performed under in situ conditions known to those skilled in the art.

A number of fluorescent labels are known in the art and include DAPI, Cy3, Cy3.5, Cy5, CyS.5, Cy7, umbelliferone, fluorescein, fluorescein isothiocyanate (FITC), rhodamine, dichlorotriazinylamine fluorescein, dansyl chloride or phycoerythrin. A fluorescent label should have distinguishable excitation and emission spectra. Where two or more fluorescent labels are used, they should have differing excitation and emission spectra that differ, respectively, by some minimal value (typically about 15-30 nm). The degree of difference will typically be determined by the types of filters being used in the process. Typical excitation and emission spectra for DAPI, FITC, Cy3, Cy3.5, Cy5, Cy5.5, and Cy7 are provided below in table 1.

TABLE 1

| Fluorescent indicator | Excitation Peak | Emission Peak |
| --- | --- | --- |
| DAPI | 350 | 450 |
| FITC | 490 | 520 |
| Cy3 | 550 | 570 |
| Cy3.5 | 580 | 595 |
| Cy5 | 650 | 670 |
| Cy5.5 | 680 | 700 |
| Cy7 | 755 | 780 |

Once labeled, the sample is aspirated with a pipette and loaded into a chamber of the system. The chamber is loaded with a sample by pipetting the sample into the sample introduction port of the chamber. As the sample is loaded into the chamber, air escapes the chamber through the air escape port in the chamber. An exemplary sample size is 20 µl. Once the chamber is loaded with the sample, the chamber is loaded into the counting system through a slot in a housing of the system.

The cell sample in suspension within a cell counting chamber is illuminated by the bright field (BF) light source and the fluorescent (FL) light source. The light sources may be light emitting diodes. Collimators may be used for the light sources. A movable light shutter is used to block out bright field light when the system is used in fluorescent detection mode. A fluorescent light filter assembly is used to allow only the excitation light to illuminate the sample and to allow only the emission light from the sample to be imaged on the camera sensor. The camera may be a CCD camera with a thermoelectric cooling capability.

A bright-field image of the population of cells in the sample is acquired using the counting system of the invention. The bright-field image provides a cell count for the total population of cells in the sample. The system is then switched to fluorescent mode and a fluorescent image of cells is acquired. Only cells that have been bound by the fluorescently labeled agent will be visible in this mode, and thus only fluorescently labeled cells will be imaged in this mode. The fluorescent image provides a cell count for the number of cells in the population that have been bound by the fluorescently labeled agent. Each of the bright-field image and the fluorescent image can be an image of the entire sample. Alternatively, each of the bright-field image and the fluorescent image can be an image of a portion of the sample.

The concentration of the biomarker and cells that express the biomarker is then determined by comparing the total cell count obtained from the bright-field image to the cell count of fluorescently labeled cells obtained from the fluorescent image. Because the system utilizes a covered chamber having a fixed height, cell concentration can be determined from the cell count.

Determining Concentration or Number Count of Stem Cells in a Population of Cells Stem cells have the remarkable potential to develop into many different cell types in the body. Serving as a sort of repair system for the body, they can theoretically divide without limit to replenish other cells as long as the person or animal is still alive. When a stem cell divides, each new cell has the potential to either remain a stem cell or become another type of cell with a more specialized function, such as a muscle cell, a red blood cell, or a brain cell.

Stem cells have provided enormous opportunities for biomedical researchers to develop more effective therapeutic medicines to prevent, treat, and cure various diseases, because these cells have the unique property of regenerating themselves for a long period of time and also have the remarkable potential to differentiate into different kinds of functional cells. An aspect of the invention provides a method for determining a concentration of stem cells in a population of cells in a sample.

The method involves contacting a sample including stem cells with a fluorescently labeled agent that specifically binds the stem cells in the sample. Biomarkers specific to stem cells include TRA-1-81, TRA-1-60, Thy-1, SSEA-3, SSEA4, Oct-4, CD9, CD30, and alkaline phosphatase. The agent can be an antibody, a particle coated with the antibody, polypeptide, oligonucleotide, or polynucleotide that has been fluorescently labeled.

After the sample has been contacted with the fluorescently labeled agent, the sample is aspirated with a pipette and loaded into a chamber of the system. The chamber is loaded with a sample by pipetting the sample into the sample introduction port of the chamber. As the sample is loaded into the chamber, air escapes the chamber through the air escape port in the chamber. An exemplary sample size is 20 µl. Once the chamber is loaded with the sample, the chamber is loaded into the counting system through a slot in a housing of the system.

The cell sample in suspension within a cell counting chamber is illuminated by the bright field (BF) light source and the fluorescent (FL) light source. The light sources may be light emitting diodes. Collimators may be used for the light sources. A movable light shutter is used to block out bright field light when the system is used in fluorescent detection mode. A fluorescent light filter assembly is used to allow only the excitation light to illuminate the sample and to allow only the emission light from the sample to be imaged on the camera sensor. The camera may be a CCD camera with a thermoelectric cooling capability.

A bright-field image of the population of cells in the sample is acquired using the counting system of the invention. The bright-field image provides a cell count for the total population of cells in the sample. The system is then switched to fluorescent mode and a fluorescent image of cells is acquired. Only the stem cells that have been bound by the fluorescently labeled agent will be visible in this mode, and thus only stem cells will be imaged in this mode. The fluorescent image provides a cell count for the number of stem cells in the population of cells. Each of the bright-field image and the fluorescent image can be an image of the entire sample. Alternatively, each of the bright-field image and the fluorescent image can be an image of a portion of the sample.

The concentration of stem cells in the population of cells is then determined by comparing the total cell count obtained from the bright-field image to the cell count of stem cells obtained from the fluorescent image. Because the system utilizes a covered chamber having a fixed height, stem cell concentration can be determined from the cell count.

Determining Infection Rates of Malaria

Malaria is a vector-borne infectious disease caused by protozoan parasites. Malaria is one of the most common infectious diseases and an enormous public health problem. The disease is caused by protozoan parasites of the genus *Plasmodium*. Only four types of the *plasmodium* parasite can infect humans; the most serious forms of the disease are caused by *Plasmodium falciparum* and *Plasmodium vivax*, but other related species (*Plasmodium ovale, Plasmodium*

*malariae*) can also affect humans. This group of human-pathogenic *Plasmodium* species is usually referred to as malaria parasites.

Usually, people get malaria by being bitten by an infective female *Anopheles* mosquito. Only *Anopheles* mosquitoes can transmit malaria, and they must have been infected through a previous blood meal taken on an infected person. When a mosquito bites an infected person, a small amount of blood is taken that contains microscopic malaria parasites. About one week later, when the mosquito takes its next blood meal, these parasites mix with the mosquito's saliva and are injected into the person being bitten. The parasites multiply within red blood cells, causing symptoms that include light-headedness, shortness of breath, tachycardia, fever, chills, nausea, flu-like illness, and, in severe cases, coma, and death. Systems of the invention can be used to provide a simple, quick, and reliable method to identify and characterize the malaria parasitic infection rate in red blood cells.

The method involves contacting a sample of red blood cells from a subject having malaria with a fluorescently labeled agent specific for the malaria parasites. Red blood cells do not contain nucleic acid (DNA or RNA), while the malaria parasites do contain nucleic acid. Because red blood cells do not contain nucleic acid, the fluorescently labeled agent should be a cell permeable nucleic acid selective fluorescent dye, such as acridine orange (commercially available from Fluka Bio-Chemica, Buchs, Switzerland), that will label nucleic acid in the malaria parasites while not labeling non-infected red blood cells.

After the sample has been contacted with the fluorescently labeled agent, the sample is aspirated with a pipette and loaded into a chamber of the system. The chamber is loaded with a sample by pipetting the sample into the sample introduction port of the chamber. As the sample is loaded into the chamber, air escapes the chamber through the air escape port in the chamber. An exemplary sample size is 20 µl. Once the chamber is loaded with the sample, the chamber is loaded into the counting system through a slot in a housing of the system.

The cell sample in suspension within a cell counting chamber is illuminated by the bright field (BF) light source and the fluorescent (FL) light source. The light sources may be light emitting diodes. Collimators may be used for the light sources. A movable light shutter is used to block out bright field light when the system is used in fluorescent detection mode. A fluorescent light filter assembly is used to allow only the excitation light to illuminate the sample and to allow only the emission light from the sample to be imaged on the camera sensor. The camera may be a CCD camera with a thermo-electric cooling capability.

A bright-field image of the population of red blood cells in the sample is acquired using the counting system of the invention. The bright-field image provides a cell count for the total population of red blood cells in the sample, i.e., infected red blood cells and non-infected red blood cells. The system is then switched to fluorescent mode and a fluorescent image of red blood cells is acquired. Only the red blood cells that have been infected with a malaria parasite will be visible in this mode, and thus only malaria infected red blood cells will be imaged in this mode. The fluorescent image provides a cell count for the number of malaria infected red blood cells in the population of red blood cells. Each of the bright-field image and the fluorescent image can be an image of the entire sample. Alternatively, each of the bright-field image and the fluorescent image can be an image of a portion of the sample.

The malaria infection rate in the population of red blood cells is then determined by comparing the total red blood cell count obtained from the bright-field image to the red blood cell count of malaria infected red blood cells obtained from the fluorescent image. Because the system utilizes a covered chamber having a fixed height, the malaria infection rate can be determined from the cell count.

Identifying and Counting Adipocytes

Adipocytes are the cells that primarily compose adipose tissue, specialized in storing energy as fat. There are two types of adipose tissue, white adipose tissue and brown adipose tissue. White fat cells or monovacuolar cells contain a large lipid droplet surrounded by a layer of cytoplasm. The nucleus is flattened and located on the periphery. A typical fat cell is 0.1 mm in diameter with some being twice that size and others half that size. The fat stored is in a semi-liquid state, and is composed primarily of triglycerides and cholesteryl ester. White fat cells secrete resistin, adiponectin, and leptin. Brown fat cells or plurivacuolar cells are polygonal in shape. Unlike white fat cells, these cells have considerable cytoplasm, with lipid droplets scattered throughout. The nucleus is round, and, although eccentrically located, it is not in the periphery of the cell. The brown color comes from the large quantity of mitochondria.

Characterization of adipocytes is generally done by light microscopy. Often it is impossible to distinguish adipocytes from lipid sphere background because they look the same. Systems of the invention can be used to provide a simple, quick, and reliable method to identify and characterize adipocytes.

The method involves contacting a sample including adipocytes with a fluorescently labeled agent that specifically binds the adipocytes. Lipid droplets do not contain nucleic acid (DNA or RNA), while the adipocytes do contain nucleic acid. Because lipid droplets do not contain nucleic acid, the fluorescently labeled agent should be a cell permeable nucleic acid selective fluorescent dye, such as acridine orange, that will label nucleic acid in the adipocytes while not effecting the lipid droplets.

After the sample has been contacted with the fluorescently labeled agent, the sample is aspirated with a pipette and loaded into a chamber of the system. The chamber is loaded with a sample by pipetting the sample into the sample introduction port of the chamber. As the sample is loaded into the chamber, air escapes the chamber through the air escape port in the chamber. An exemplary sample size is 20 µl. Once the chamber is loaded with the sample, the chamber is loaded into the counting system through a slot in a housing of the system.

The cell sample in suspension within a cell counting chamber is illuminated by the bright field (BF) light source and the fluorescent (FL) light source. The light sources may be light emitting diodes. Collimators may be used for the light sources. A movable light shutter is used to block out bright field light when the system is used in fluorescent detection mode. A fluorescent light filter assembly is used to allow only the excitation light to illuminate the sample and to allow only the emission light from the sample to be imaged on the camera sensor. The camera may be a CCD camera with a thermo-electric cooling capability.

A bright-field image of the sample is acquired using the counting system of the invention. The bright-field image provides an image of adipocytes and lipid droplets in the sample. The system is then switched to fluorescent mode and a fluorescent image of adipocytes is acquired. Only the adipocytes will be visible in this mode, and thus only adipocytes will be imaged in this mode. The fluorescent image provides a cell count for the number of adipocytes in the sample. Each of the bright-field image and the fluorescent image can be an image of the entire sample. Alternatively, each of the bright-field image and the fluorescent image can be an image of a portion of the sample. The adipocytes are identified by comparing the bright-field image to the fluorescent image.

Detecting a Biomolecule in a Sample

Systems of the invention can be used to provide a simple, quick, and reliable method to quantitatively profile biomolecules from biological samples, such as serum, cell culture supernatant, or cell lysis. Biomolecules include proteins, polynucleotides (e.g., DNA or RNA), organic material, and any combination of the foregoing.

The method involves contacting a sample with particles coated with a biotinylated antibody, and streptavidin coupled to a fluorescent indicator. Exemplary particle sizes include 5 µm, 10 µm, 15 µm, 20 µm, 25 µm, 30 µm, 35 µm, 40 µm, 45 µm, 50 µm. The particle can be composed of any material. Exemplary particles include gold particles, latex particles, glass particles, or magnetic particles. These particles can be coated with a biotinylated antibody that has specificity for the biomolecule of interest in the sample. Methods for coupling biotin to antibodies is well known in the art, see for example Stanley (Essentials in Immunology and serology, Delmar, pp. 152-153, 2002). Methods for coating particles with biotinylated antibodies is well known in the art, see for example Harlow et al., Antibodies, Cold Spring Harbor Laboratory, 1988).

Once the sample has been contacted with the particles coated with a biotinylated antibody, and streptavidin coupled to a fluorescent indicator, the sample is aspirated with a pipette and loaded into a chamber of the system. The chamber is loaded with a sample by pipetting the sample into the sample introduction port of the chamber. As the sample is loaded into the chamber, air escapes the chamber through the air escape port in the chamber. An exemplary sample size is 20 µl. Once the chamber is loaded with the sample, the chamber is loaded into the counting system through a slot in a housing of the system.

The cell sample in suspension within a cell counting chamber is illuminated by the bright field (BF) light source and the fluorescent (FL) light source. The light sources may be light emitting diodes. Collimators may be used for the light sources. A movable light shutter is used to block out bright field light when the system is used in fluorescent detection mode. A fluorescent light filter assembly is used to allow only the excitation light to illuminate the sample and to allow only the emission light from the sample to be imaged on the camera sensor. The camera may be a CCD camera with a thermoelectric cooling capability.

A bright-field image of the sample is acquired using the counting system of the invention. The bright-field image acts as a control, providing an image of particles and biomolecules bound to the biotinylated antibody particle/streptavidin coupled fluorescent indicator complex. The system is then switched to fluorescent mode and a fluorescent image of multiplex binding activity of the biomolecules to the biotinylated antibody particle/streptavidin coupled fluorescent indicator complex is acquired. The fluorescent image provides a count for the number of biomolecules bound to the biotinylated antibody particle/streptavidin coupled fluorescent indicator complex. Each of the bright-field image and the fluorescent image can be an image of the entire sample. Alternatively, each of the bright-field image and the fluorescent image can be an image of a portion of the sample. The biomolecules bound to the biotinylated antibody particle/streptavidin coupled fluorescent indicator complex are identified by comparing the bright-field image to the fluorescent image. The combination of bright-field imaging and fluorescent imaging allows for monitoring and control of the number of reaction particles to ensure consistent data.

Determining Concentration or Number Count of Viable Hepatocytes

The liver consists of two main lobes, both of which are made up of thousands of lobules. The liver regulates most chemical levels in the blood and excretes a product called bile that helps carry away waste products from the liver. All blood leaving the stomach and intestines passes through the liver. The liver processes this blood and breaks down nutrients and drugs into forms that are easier to use for the rest of the body. More than 500 vital functions have been identified with the liver. Some of these functions include: production of bile; production of certain proteins for blood plasma; production of cholesterol and special proteins to help carry fats through the body; conversion of excess glucose into glycogen for storage; regulation of blood levels of amino acids; processing of hemoglobin for use of its iron content; conversion of poisonous ammonia to urea; clearing the blood of drugs and other poisonous substances; regulating blood clotting; and resisting infections by producing immune factors and removing bacteria from the blood stream.

There are many disorders of the liver that require clinical care by a physician or other healthcare professional. According to the American Liver Foundation, more than 15 million people in the United States suffer from liver diseases, and more than 43,000 die of a liver disease each year.

Figure 6:
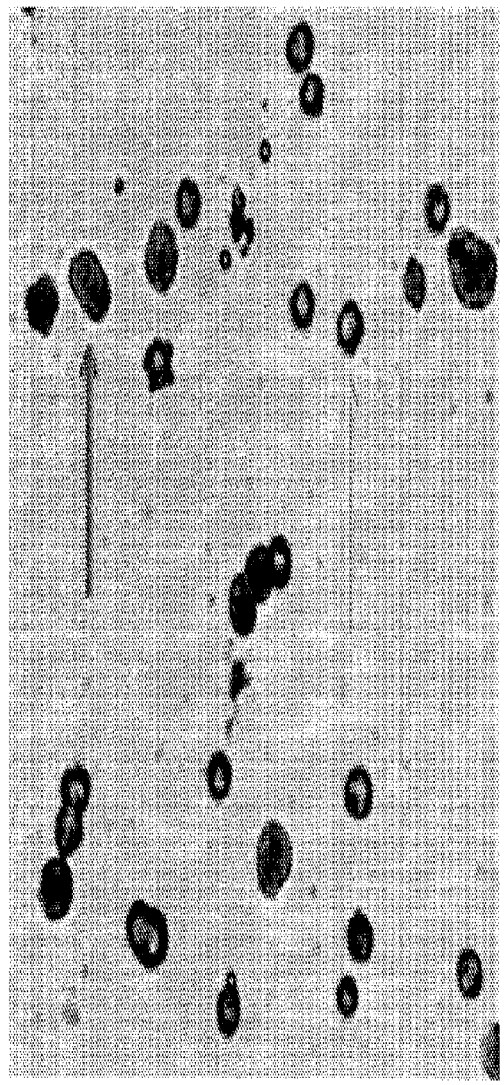
FIG. 6 is a picture showing hepatocytes stained with trypan blue.
Figure 7:
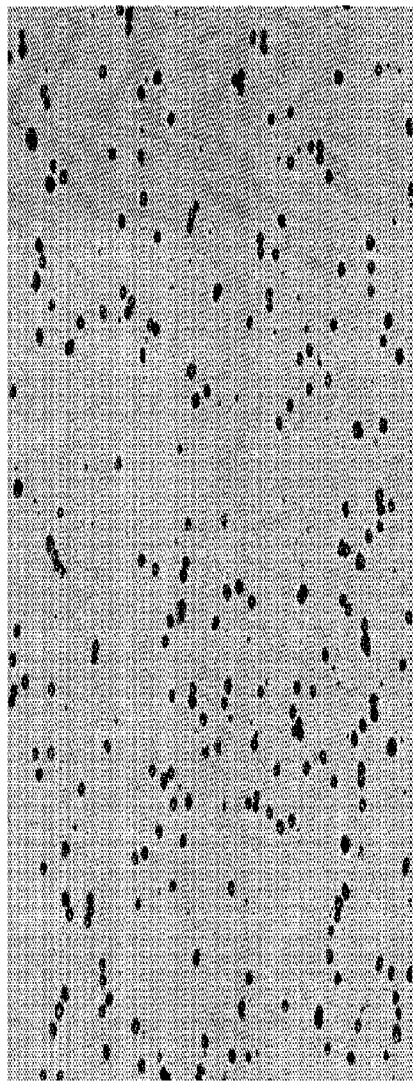
FIG. 7 is a picture showing fluorescently stained hepatocytes.
Figure 8:
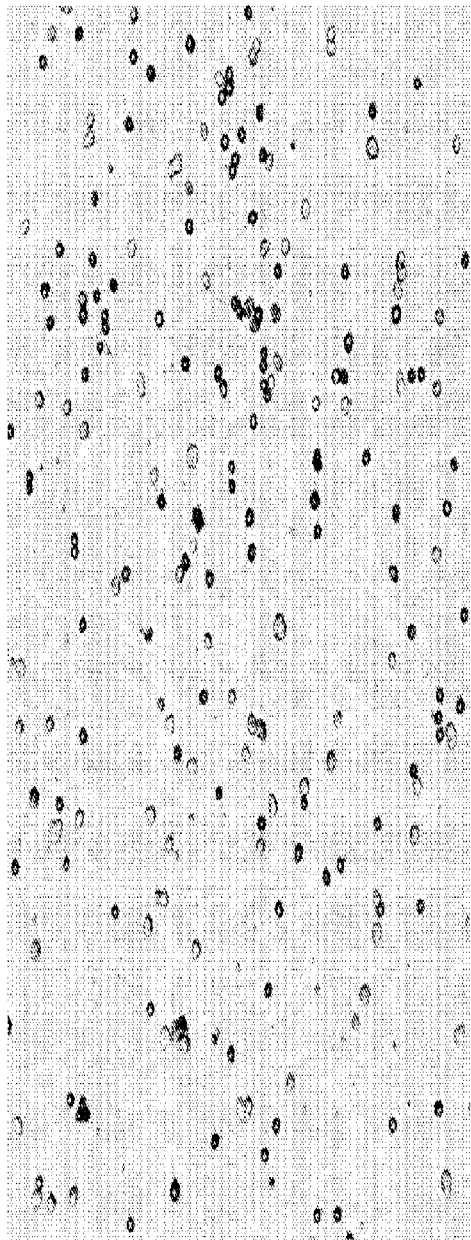
FIG. 8 is another picture showing fluorescently stained hepatocytes.
Figure 9:
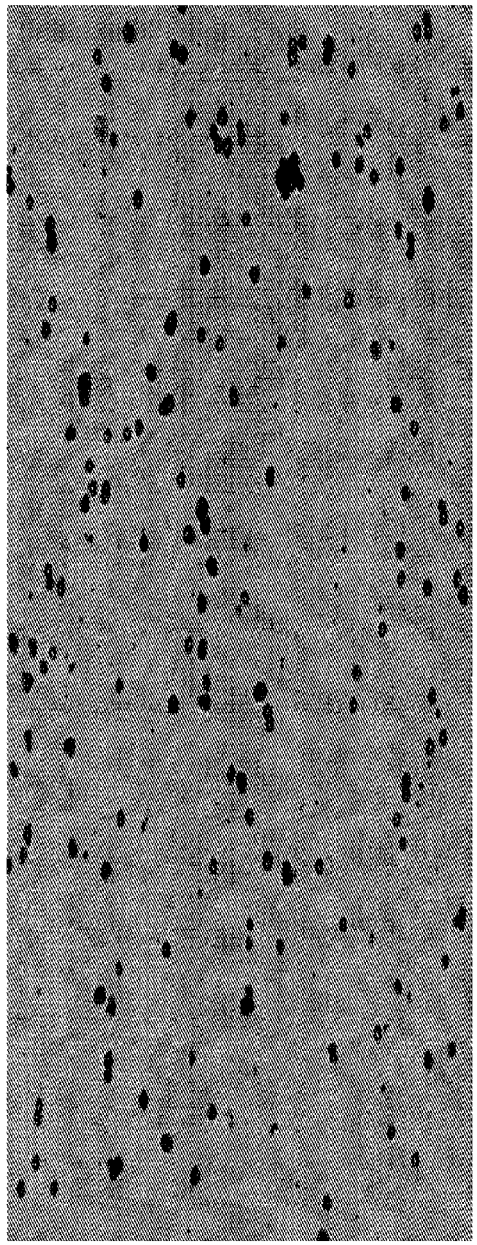
FIG. 9 is another picture showing fluorescently stained hepatocytes.
Figure 10:
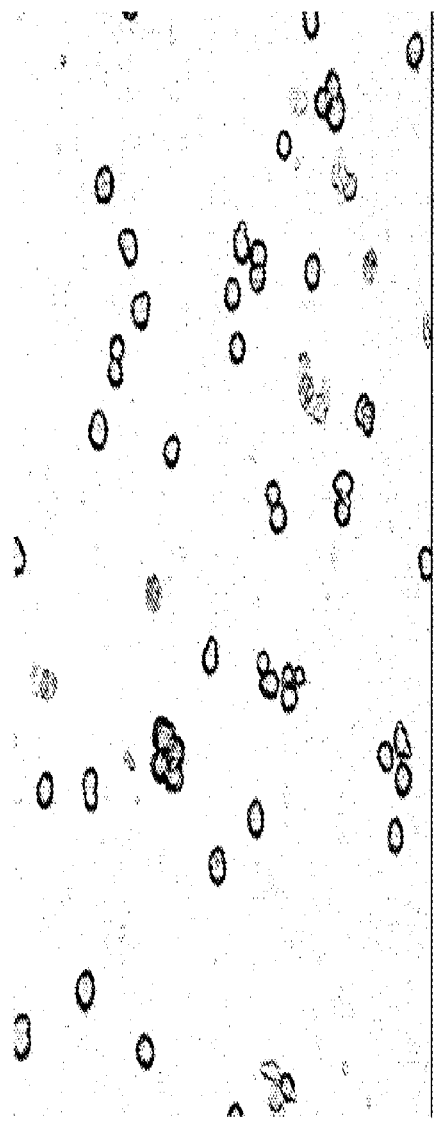
FIG. 10 is a picture showing hepatocytes imaged under bright-field.
Figure 11:
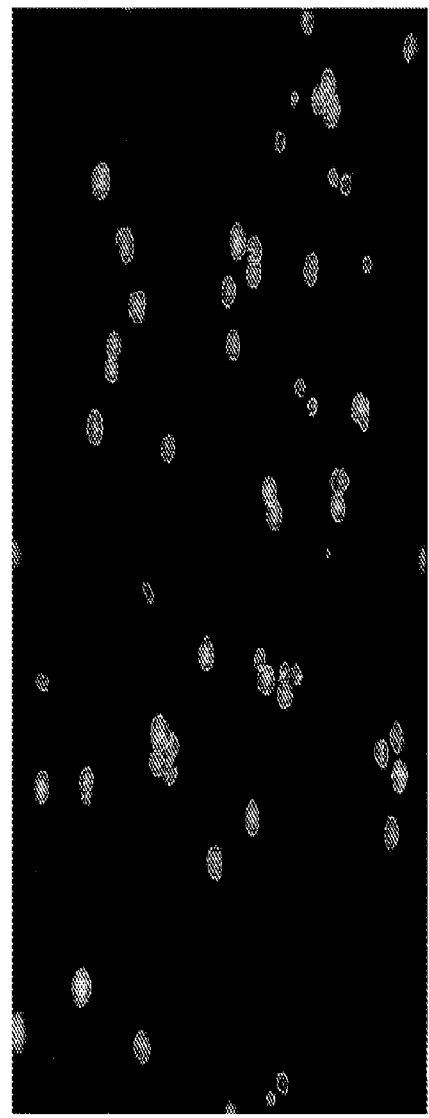
FIG. 11 is another picture showing fluorescently stained hepatocytes.
Figure 12:
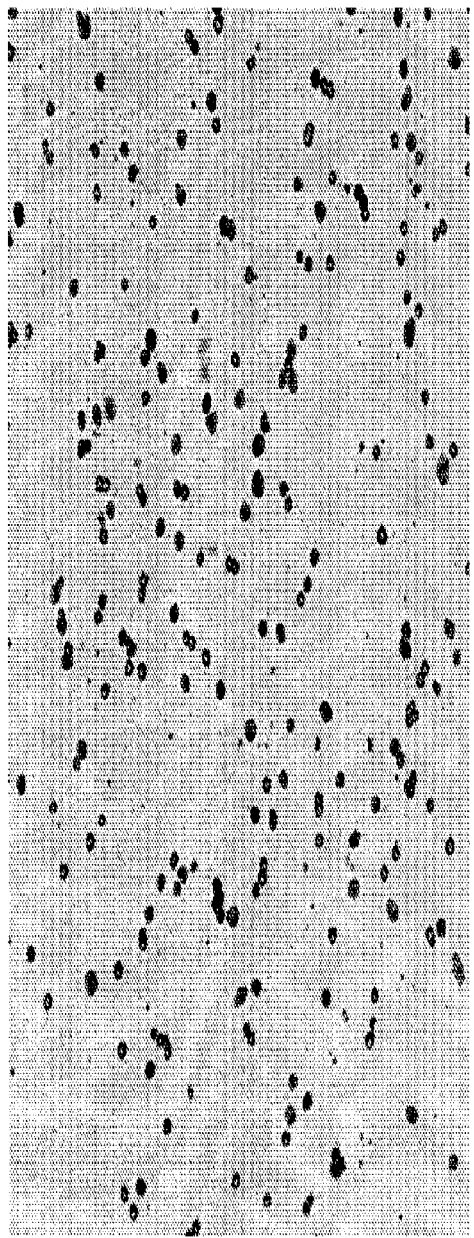
FIG. 12 is another picture showing fluorescently stained hepatocytes.
Figure 13:
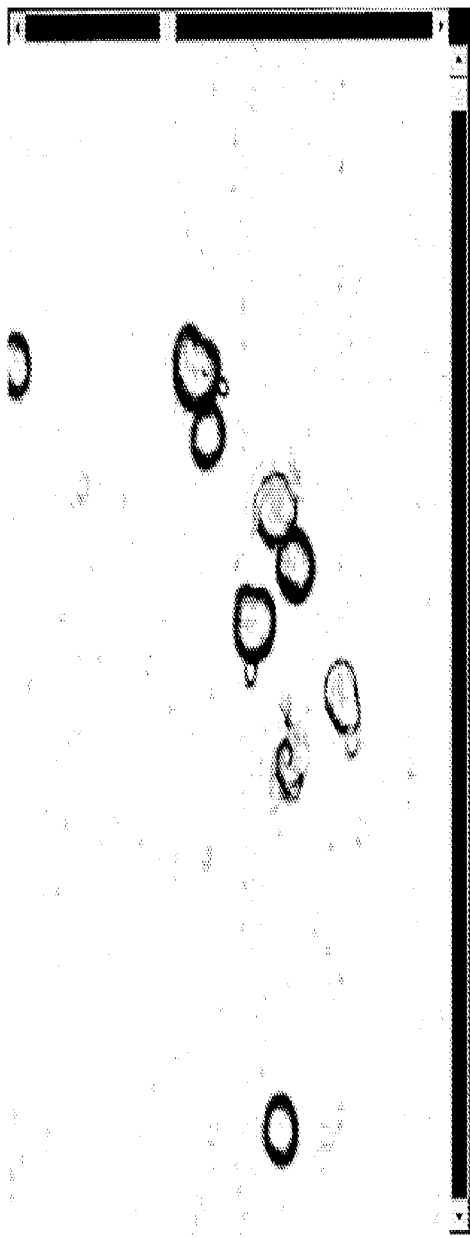
FIG. 13 is a picture showing hepatocytes that have been magnified and imaged under bright-field.
Figure 14:
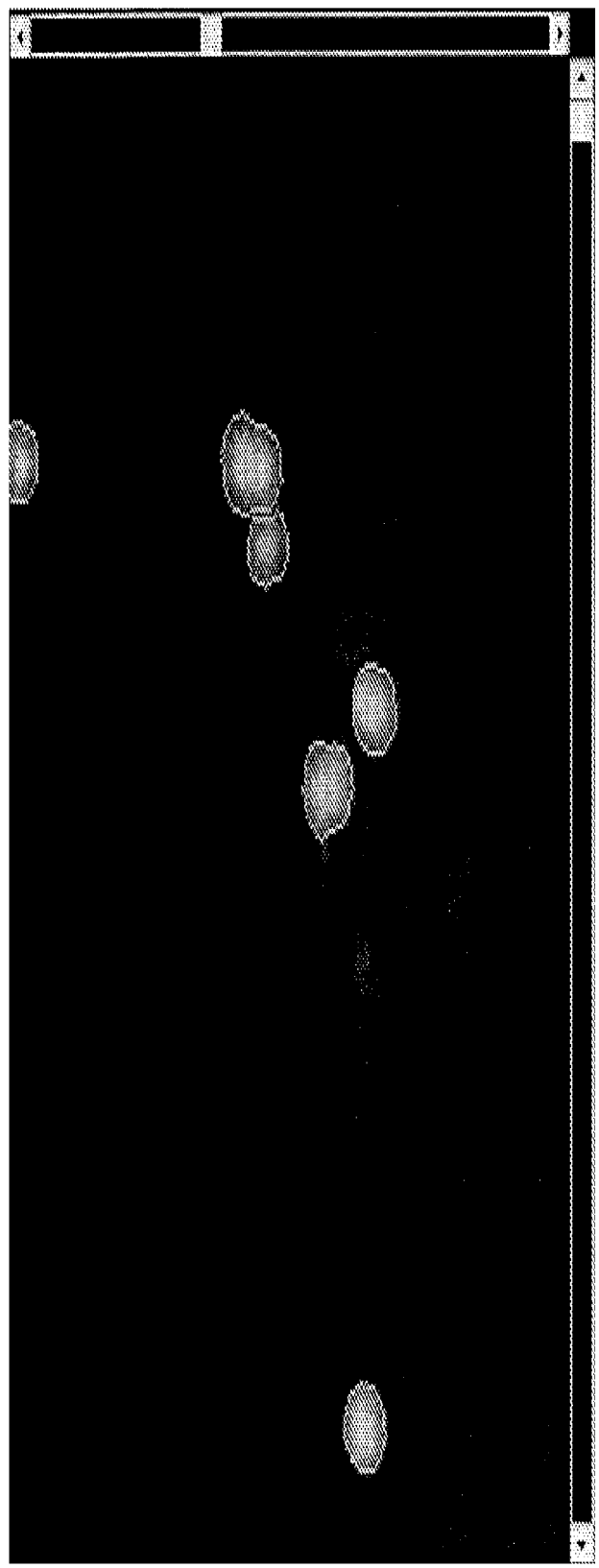
FIG. 14 is a picture showing hepatocytes that have been magnified and fluorescently imaged.

Currently, researchers stain primary hepatocytes with trypan blue and manually count dead cells and live cells under a microscope in a bright-field configuration. The viability of sample is calculated using manual counted live cells vs. trypan blue stained dead cells. As shown in FIG. 6, two populations were observed that represent live and dead cells with green and blue arrow respectively. There are technical difficulties with automation of the trypan blue viability test because of intracellular structures, inconsistencies of cell images, variations between species to species and sample to sample, and declustering. In addition, it has been reported that there are staining variations between different primary hepatocytes, such as species-to-species, sample-to-sample, and process-to-process. This variation makes the counting results inconsistent.

Systems of the invention provide a quick, simple, and reliable method for determining the concentration of viable hepatocytes cells in a population of hepatocytes in a sample. The concentration of viable hepatocytes cells in a population of hepatocytes in a sample can be correlated with a particular liver disease or disease state. The sample can include primary fresh hepatocytes, prior to cryopreservation. The sample can also include post-thaw hepatocytes, thawed post cryopreservation.

The method involves contacting a sample including hepatocytes with at least one fluorescently labeled agent. If two fluorescently labeled agents are used, the fluorescently labeled agents should have different fluorescence characteristics, i.e., different excitation wavelengths and different emission wavelengths. When two fluorescently labeled agents are used, one can be acridine orange and the other can be propidium iodine (PI). Using these tandem agents, acridine orange stains viable hepatocytes while PI stains dead hepatocytes. PI is commercially available from, for example, Fluka BioChemica (Buchs, Switzerland). PI is an intercalating agent that fluoresces when bound to DNA. PI is membrane impermeant and excluded from viable cells, thus PI is commonly used to identify and/or determine the amount of non-living cells in a mixed population.

Once the sample has been contacted with the fluorescently labeled agent, the sample is aspirated with a pipette and loaded into a chamber of the system. The chamber is loaded with a sample by pipetting the sample into the sample introduction port of the chamber. As the sample is loaded into the chamber, air escapes the chamber through the air escape port in the chamber. An exemplary sample size is 20 μl. Once the chamber is loaded with the sample, the chamber is loaded into the counting system through a slot in a housing of the system.

The cell sample in suspension within a cell counting chamber is illuminated by the bright field (BF) light source and the fluorescent (FL) light source. The light sources may be light emitting diodes. Collimators may be used for the light sources. A movable light shutter is used to block out bright field light when the system is used in fluorescent detection mode. A fluorescent light filter assembly is used to allow only the excitation light to illuminate the sample and to allow only the emission light from the sample to be imaged on the camera sensor. The camera may be a CCD camera with a thermoelectric cooling capability.

Two or more images of the sample are acquired using the counting system of the invention. The first and second image are selected from the group consisting of a bright-field image, a fluorescent image of viable hepatocytes, and a fluorescent image of dead hepatocytes, in which the first image is different from the second image. The bright-field image provides an image of the total cell count, i.e., viable and dead cells, of the population of hepatocytes. The system is then switched to fluorescent mode and fluorescent images are acquired. The first fluorescent image acquired by a first fluorescent channel of the counting system will be a fluorescent image of hepatocytes fluorescently labeled with acridine orange. This image provides a cell count of viable hepatocytes in the population of hepatocytes. The second fluorescent image acquired by a second fluorescent channel of the counting system will be a fluorescent image of hepatocytes labeled with PI. This image provides a cell count of dead hepatocytes in the population of hepatocytes. FIGS. 7-14 show hepatocytes stained with different fluorescent agents, e.g., acridine orange and PI, and imaged under different conditions, bright-field and two different fluorescent lights. Each of the bright-field image and the fluorescent images can be an image of the entire sample. Alternatively, each of the bright-field image and the fluorescent images can be an image of a portion of the sample.

The concentration of viable hepatocytes can then be determined by numerous counting methods. Because the system utilizes a covered chamber having a fixed height, cell concentration can be determined from the cell count. When the first image is the fluorescent image of live hepatocytes and the second image is the fluorescent image of dead hepatocytes, the concentration of viable hepatocytes in the population of hepatocytes is determined by comparing cell count from the fluorescent image of live hepatocytes to cell count from the fluorescent image of dead hepatocytes. Alternatively, when the first image is the bright-field image and the second image is the fluorescent image of dead hepatocytes, the concentration of viable hepatocytes in the population of hepatocytes is determined by comparing cell count from the bright-field image to cell count from the fluorescent image of dead hepatocytes. Alternatively, when the first image is the bright-field image and the second image is the fluorescent image of live hepatocytes, the concentration of viable hepatocytes in the population of hepatocytes is determined by comparing cell count from the bright-field image to cell count from the fluorescent image of live hepatocytes.

Alternatively, three images can be acquired by the system, a bright-field image, a fluorescent image of viable hepatocytes, and a fluorescent image of dead hepatocytes. The bright-field image provides an image of the total cell count, i.e., viable and dead cells, of the population of hepatocytes. The fluorescent image of hepatocytes fluorescently labeled with acridine orange provides a cell count of viable hepatocytes in the population of hepatocytes. The fluorescent image of hepatocytes labeled with PI a cell count of dead hepatocytes in the population of hepatocytes. The concentration of viable hepatocytes can then be determined by comparing the cell count from bright-field image with the cell count from the two fluorescent images.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for determining a concentration of cells that express a biomarker in a population of cells in a liquid sample comprising:
   contacting a liquid sample comprising cells that express a biomarker with a fluorescently labeled agent that specifically binds the biomarker;
   loading the liquid sample into a covered sample chamber having a known height and configured to hold a known volume of the liquid sample, containing a static population of cells wherein the population of cells is suspended within the sample chamber;
   acquiring a single static bright-field image of the population of cells in the known volume of the liquid sample in the sample chamber;
   acquiring a single static fluorescent image of the population of cells with the fluorescently labeled agent bound thereto in the known volume of the liquid sample in the sample chamber; and
   analyzing the single static bright-field image and the single static fluorescent image in relation to the known volume of the liquid sample to determine the concentration of cells that express the biomarker in the population of cells.

2. The method according to claim 1, wherein prior to said contacting step, the method further comprises contacting the population of cells with an agent that makes the population of cells permeable.

3. The method according to claim 1, wherein the biomarker is a cell surface biomarker.

4. The method according to claim 1, wherein the biomarker is an intercellular biomarker.

5. The method according to claim 1, wherein the fluorescently labeled agent specifically binds to a specific epitope of the biomarker.

6. The method according to claim 1, consisting essentially of:

contacting a liquid sample comprising cells that express a biomarker with a fluorescently labeled agent that specifically binds the biomarker;

loading the liquid sample into a covered sample chamber having a known height and configured to hold a known volume of the liquid sample, wherein the population of cells is suspended within the sample chamber;

acquiring a single static bright-field image of the population of cells in the known volume of the liquid sample in the sample chamber;

acquiring a single static fluorescent image of the population of cells with the fluorescently labeled agent bound thereto in the known volume of the liquid sample in the sample chamber; and analyzing the single static bright-field image and the single static fluorescent image in relation to the known volume of the liquid sample to determine the concentration of cells that express the biomarker in the population of cells.

7. The method according to claim 6, wherein the biomarker is a cell surface biomarker.

8. The method according to claim 6, wherein the biomarker is an intercellular biomarker.

9. The method according to claim 6, wherein the fluorescently labeled agent specifically binds to a specific epitope of the biomarker.

10. A method for determining a concentration of stem cells in a population of cells in a liquid sample comprising:

contacting a liquid sample comprising stem cells with a fluorescently labeled agent that specifically binds the stem cells in the liquid sample;

loading the liquid sample into a covered sample chamber having a known height and configured to hold a known volume of the liquid sample, containing a static population of cells wherein the population of cells is suspended within the sample chamber;

acquiring a single static bright-field image of the population of cells in the known volume of the sample in the sample chamber;

acquiring a single static fluorescent image of the population of cells with the fluorescently labeled agent bound thereto in the known volume of the sample in the sample chamber; and analyzing the single static bright-field image and the single static fluorescent image in relation to the known volume of the liquid sample to determine the concentration of stem cells in the population of cells.

11. The method according to claim 10, wherein the fluorescently labeled agent is a fluorescently labeled antibody specific for a stem cell, or a particle coated with a fluorescently labeled antibody specific for a stem cell.

12. The method according to claim 10, wherein the biomarker is selected from the group consisting of TRA-1-81, TRA-I-60, Thy-1, SSEA-3, SSEA4, Oct-4, CD9, CD30, and alkaline phosphatase.

13. The method according to claim 10, consisting essentially of:

contacting a liquid sample comprising stem cells with a fluorescently labeled agent that specifically binds the stem cells in the liquid sample;

loading the liquid sample into a covered sample chamber having a known height and configured to hold a known volume of the liquid sample, wherein the population of cells is suspended within the sample chamber;

acquiring a single static bright-field image of the population of cells in the known volume of the sample in the sample chamber;

acquiring a single static fluorescent image of the population of cells with the fluorescently labeled agent bound thereto in the known volume of the sample in the sample chamber; and analyzing the single static bright-field image and the single static fluorescent image in relation to the known volume of the liquid sample to determine the concentration of stem cells in the population of cells.

14. The method according to claim 13, wherein the fluorescently labeled agent is a fluorescently labeled antibody specific for a stem cell, or a particle coated with a fluorescently labeled antibody specific for a stem cell.

15. The method according to claim 14, wherein the biomarker is selected from the group consisting of TRA-1-81, TRA-I-60, Thy-1, SSEA-3, SSEA4, Oct-4, CD9, CD30, and alkaline phosphatase.

16. A method for determining a concentration of adipocytes among cells in liquid sample comprising:

contacting a liquid sample comprising adipocytes with a fluorescently labeled agent that specifically binds the adipocytes;

loading the liquid sample into a covered sample chamber having a known height and configured to hold a known volume of the liquid sample, containing a static population of cells wherein the cells are suspended within the covered sample chamber;

acquiring a single static bright-field image of the population of cells in the known volume of the sample in the covered sample chamber;

acquiring a single static fluorescent image of the population of cells with the fluorescently labeled agent bound thereto in the known volume of the sample in the covered sample chamber; and analyzing the single static bright-field image and the single static fluorescent image in relation to the known volume of the liquid sample to determine the concentration of adipocytes in the population of cells.

17. The method of claim 16, consisting essentially of:

contacting a liquid sample comprising adipocytes with a fluorescently labeled agent that specifically binds the adipocytes;

loading the liquid sample into a covered sample chamber having a known height and configured to hold a known volume of the liquid sample, wherein the cells are suspended within the covered sample chamber;

acquiring a single static bright-field image of the population of cells in the known volume of the sample in the covered sample chamber;

acquiring a single static fluorescent image of the population of cells with the fluorescently labeled agent bound thereto in the known volume of the sample in the covered sample chamber; and analyzing the single static bright-field image and the single static fluorescent image in relation to the known volume of the liquid sample to determine the concentration of adipocytes in the population of cells.

* * * * *